United States Patent [19]

Matsui et al.

[11] Patent Number: 5,161,972
[45] Date of Patent: Nov. 10, 1992

[54] METHOD AND MAGNETIC DEVICE FOR FIXING A DENTURE

[75] Inventors: Yasuhiro Matsui; Kazuhiko Fukamachi, both of Kanagawa, Japan

[73] Assignee: Nippon Mining Co., Ltd., Tokyo, Japan

[21] Appl. No.: 575,743

[22] Filed: Aug. 31, 1990

[30] Foreign Application Priority Data

Sep. 4, 1989 [JP] Japan .................. 1-227507
Aug. 14, 1990 [JP] Japan .................. 2-213736

[51] Int. Cl.$^5$ .................................. A61C 13/235
[52] U.S. Cl. .................................. 433/189
[58] Field of Search .......................... 433/189

[56] References Cited

U.S. PATENT DOCUMENTS

| | | | |
|---|---|---|---|
| 4,530,663 | 7/1985 | Portnoy | 433/189 |
| 4,814,027 | 3/1989 | Masumoto et al. | 148/300 |
| 4,824,371 | 4/1989 | Deutsch et al. | 433/189 |
| 4,911,640 | 3/1990 | Schwab | 433/189 |

FOREIGN PATENT DOCUMENTS

| | | |
|---|---|---|
| 3431190 | 3/1986 | Fed. Rep. of Germany . |
| 3439955 | 5/1986 | Fed. Rep. of Germany ...... 433/189 |
| 0047356 | 4/1980 | Japan .................. 433/189 |

OTHER PUBLICATIONS

"Good News from Your Dentist", Mechanics Illustrated, Mar. 1968, pp. 69-70.
Press Release, "Trial Production and Sales of Platinum Magnet" (Dec. 11, 1989).
Weekly Toyo Keizai (Feb. 3, 1990).
"Mass Production of Platinum Magnets", New Technology Japan, vol. 17, No. 12 (Mar. 1990).
"Nippon offers new magnet", Nippon Mining Catalogue, (Jan. 1990).

Primary Examiner—John J. Wilson
Attorney, Agent, or Firm—Armstrong & Kubovcik

[57] ABSTRACT

In a method and device for fixing a denture to the root cap, which is embedded in the tooth root, non-plated platinum magnet containing from 33–47% of Pt is attached to the inner or lower surface of the denture so as to generate the magnetic retention between the magnet and the root cap.

7 Claims, 1 Drawing Sheet

METHOD AND MAGNETIC DEVICE FOR FIXING A DENTURE

BACKGROUND OF INVENTION

1. Field of Invention

The present invention relates to a method and device for fixing a denture.

2. Description of Related Art

Research on denture-fixing by a magnet is being made widely not only in Japan but also in various countries. According to the fixing method, a rare-earth magnet of the $SmCo_5$ or $Sm_2Co_{17}$ type is attached to the inner or bottom surface of the denture and is magnetically fixed to the root cap which is made of a Fe-Cr based corrosion-resistant stainless steel having soft magnetic property and which is embedded in the tooth root in mouth (c.f., FINITE ELEMENT ANALYSIS OF MAGNET DEVICES WITH A CUP YOKE FOR RETAINING A DENTURE, Y. Kinouchi et al, Paper No. 17P0407 at the 10th International Workshop on Rare-Earth Magnets and Their Applications, Kyoto, Japan, 16-19, May 1989, pp 157-158).

BRIEF DESCRIPTION OF DRAWINGS

Referring to FIG. 1, a rare-earth magnet 1 (hereinafter referred to as the magnet 1) is rigidly mounted in the chamber 2. The chamber 2 consists of the chamber body 2a in the form of a cup, which has also functions as a yoke and corrosion-proof cup. After the magnet 1 is encapsulated, the open lower side of the chamber body 2a is welded to the cover 2b at the fringe. Both the chamber body 2a and the cover 2b consist of corrosion-resistant stainless steel having soft magnetic property. The yoke 2 is bonded to the inner surface of the denture 3 which consists of the artificial tooth 3. The denture 3 may be referred to as an upper denture. The denture base is denoted by 4. The root cap 5 is made of corrosion-resistant stainless steel having soft magnetic property. The root cap 5 is threaded and is screwed into the root 6. The gum is denoted by 7. Before fixing the denture 3 to the root cap 5, a gap 8 is formed inbetween. The magnet 1 and the root cap 5 are rigidly fixed to one another by the magnetic retention. The N(S) and S(N) poles of the magnet 1 are positioned on the top and bottom surfaces of the magnet, respectively. The magnetic flux between the N and S poles passes through the root cap 5 and the yoke 2a. The cover 2b may or may not be in rigid contact with the root cap 5, because the magnetic flux passing through the yoke 2a and root cap 5 generates the fixing force.

Figure 1:
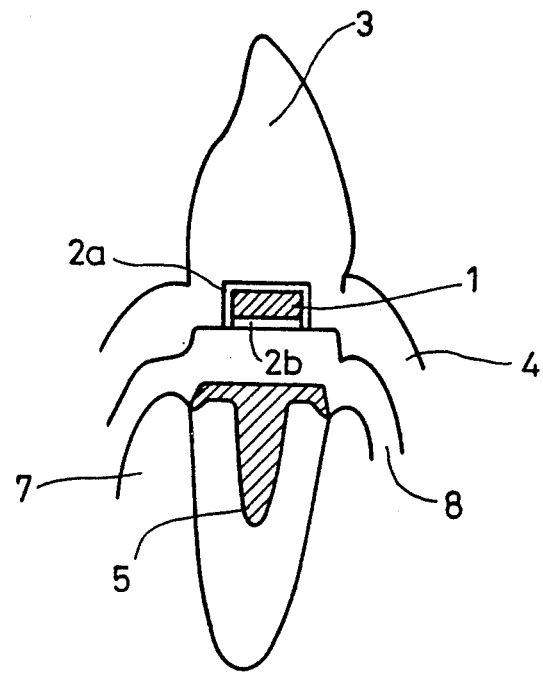
FIG. 1 illustrates a method for fixing the denture by a rare-earth magnet according to prior art.

In the initial stage of research, a ferrite magnet and an alnico magnet were considered. It turned out, however, that their magnetic retention is disadvantageously weak. It was necessary to increase the size of the magnet in order to compensate for the disadvantage. The problem arose, therefore, that a magnet of that size could not be kept within the denture.

Since the above described rare-earth magnet is small-sized and strong, a magnet small enough to be kept in the denture can attain the magnetic force required to fix the denture. However, the rare-earth magnet involves problems. That is, the corrosion resistance of the rare-earth magnet is considerably lower compared with other metallic magnets, so that the rare-earth magnet cannot withstand the severe corrosive environment in the mouth without a surface coating on the magnet. In addition, the rare-earth magnet in itself is brittle, so that it easily breaks or cracks during handling, grinding or mounting in the denture.

Researches are being made to overcome these problems by application of a Ni plating on the surface of the rare-earth s magnet or sealing the magnet in a small chamber which is made of corrosion resistant stainless steel. The magnet is set in the stainless chamber and a cap made of stainless steel is welded to the chamber body.

Ni used for the above described plating method involves a problem in that it causes allergic reaction in some patients; Sm and Co, which are components of the magnet, may be dissolved from the magnet and absorbed by the human body, when corrosion of the magnet arises due to pinholes and cracks formed in the plating layer. It has not yet been medically concluded whether or not Sm and Co are toxic to the human body. More seriously, when the corrosion of a magnet starts, the performance, specifically the coercive force of the magnet, rapidly deteriorates so that the magnet is no longer effective in fixing a denture.

In the case of sealing a magnet in a chamber of stainless steel, there are serious problems, namely, the process for is mounting the magnet in the chamber is difficult; the magnetic force between the magnet in a denture and a root cap made of soft magnetic material and embedded in the gum is weakened because the distance between them is enlarged by the corresponding thickness of the chamber. Moreover, the part of the chamber affected by the welding heat acts as the starting point of the corrosion.

Although the $SmCo_5$ or $Sm_2Co_{17}$ type magnet has sufficient magnetic performance for general application, their application for fixing a denture is considerably difficult due to the corrosion problem.

SUMMARY OF THE INVENTION

It is, therefore, an object of the present invention to provide a method and device for fixing a denture without the aid of plating on a magnet or sealing a magnet in a chamber, the latter method albeit capable of preventing the corrosion problem of the magnet.

The present inventors conceived that the so-called platinum magnet, which is magnetically as strong as the Sm-Co based rare-earth magnet and which is non-toxic to the human body. The present inventors carried out a corrosion-resistance test of the platinum magnet in a severe corrosive environment which simulates the interior of a human mouth.

In accordance with the objects of the present invention, there is provided a method for fixing a denture, comprising: attaching a non-plated magnet containing from 33 to 47 atomic % of platinum, the balance being iron, to an inner surface or lower surface of the denture; embedding in a tooth root a root cap consisting to soft magnetic, Fe-Cr based stainless steel; and, generating magnetic retention between the magnet and the root cap, thereby fixing the denture to the root cap.

In another method for fixing a denture, the magnet contains from 33 to 47 atomic % of platinum, and from 0.1 to 10 atomic % of at least one element selected from the group consisting of Ti, Mo, Nb, Ta, W, Cr, and V, the balance being iron.

In accordance with the objects of the present invention, there is also provided a device for fixing a denture comprising: a non-plated magnet bearable in a denture and a root cap fixable in a tooth-root, said magnet being attachable to an inner or lower surface of the denture and containing from 33 to 47 atomic % of platinum, the balance being iron; and, the root cap consisting of soft magnetic, Fe-Cr based stainless steel.

The magnet used for fixing a denture in accordance with the present invention contains from 33 to 47 atomic % of platinum, and preferably from 0.1 to 10 atomic % of at least one element selected from the group consisting of Ti, Mo, Nb, Ta, W, Cr, and V. The performance of this magnet is, for example, 10-11 kGauss of the residual flux density, 4.5-5.5 kOe of coercive force, and from 20-25 MGOe of the maximum energy product. This performance is virtually as high as that of the Sm-Co based rare-earth magnet. The composition of the magnet is specified in the light of its application to fixing a denture. When the platinum content is less than 33 atomic %, the maximum energy product is as low as 4 MGOe so that the denture cannot be fixed satisfactorily. When the platinum content is more than 47 atomic %, the residual flux density is as low as 6 kG, so that the denture cannot be fixed satisfactorily in this case either. In a preferable composition having from 0.1 to 10 atomic % of at least one element selected from the group consisting of Ti, Mo, Nb, Ta, W, Cr, and V, the time for solution treatment can be shortened. That is, the solution treatment is carried out at a temperature of from 900° to 1400° C. The holding time at the solution temperature is from 1 to 100 hours in the case of the composition without Ti, Mo, Nb, Ta, W, Cr and V, and is from 1 to 10 hours in the case of the preferable composition. In addition, there is less variance in the performance of the magnet, and, therefore, high performance required for fixing the denture is stably obtained.

The so-called platinum magnet used in the present invention exhibits a considerably high corrosion-resistance. Surface coating, such as Ni plating is necessary in the case of the rare-earth magnet but is unnecessary in the case of the so-called platinum magnet.

The most important feature of the present invention lies in the fundamental elements of the so-called platinum magnet, i.e., platinum and iron are not at all toxic to the human body. Since platinum and iron have a long history of medical use, it can be concluded that although their application fields are different from one another, i.e., platinum has been used for crown of teeth, and iron has been used for medicine for a long time, their combined use in a magnet would be entirely non-toxic.

The so-called platinum magnet is worked as follows, when it is to be used for fixing a denture.

First, a high frequency-induction melting under vacuo is carried out, and then the obtained molten metal is cast into a small-sized ingot-case to produce a bar having a square cross-section. The ingot is subjected to solution treatment under vacuo or in inert-gas atmosphere at a temperature of from 900° to 1400 ° C. for 1 minute to 100 hours. Then, water- or oil-cooling is immediately carried out. Pieces are then cut from the ingot treated as above and subjected to heat treatment at a temperature of from 450° to 800° C. for 1 minute to 100 hours under vacuo or in inert-gas atmosphere, followed by cooling. The pieces are then finished by machining. The finished pieces are then magnetized in a direct-current magnetic field of 2 Tesla or more, so as to generate the N and S poles on the side facing the denture and the opposite side. For reference, the heat treatment of the platinum magnet is described in detail in U.S. Pat No. 4,396,441.

The present invention is hereinafter described in detail with reference to the examples.

EXAMPLE 1

An alloy having a composition of 39.0 atomic % of platinum, the balance being iron, was melted under vacuo in a high-frequency induction furnace. An ingot having a square cross section was produced. The ingot was solution-treated under vacuo at a temperature of 1250° C. for 5 hours, followed by quenching in oil. A piece 4 mm in length, 4 mm in width and 3 mm in thickness was cut from the ingot and was heat treated under vacuo at a temperature of 610° C. for 10 hours, followed by furnace cooling. The piece was then magnetized under a magnetic field of 2 lesla in the direction of height. The plantinum magnet was thus prepared. Another piece for measuring the magnetic properties was cut from the ingot and was treated as described above. The magnetic properties were as follows: 10.3 kGauss of residual flux density; 4.7 kOe of coercive force; and 21 MGOe of the maximum energy product. The platinum magnet was subjected to a corrosion resistance test under the following conditions. Incidentally, the test sample was polished before the test by No. 1200 emery paper so as to smooth the surface.

1) Dip in 0.1 % $Na_2S$ solution (37° C.) for 3 days; and then inspection of the appearance with naked eye.
2) Dip in a 5 % NaCl +2 % $H_2O_2$ solution (40° C.); and then inspection of the appearance with naked eye and measurement of the corrosion weight-loss The results are shown in Table 1.

TABLE 1

| | | Results of Corrosion Test | | |
|---|---|---|---|---|
| | | | 5% NaCl + 2% $H_2O_2$ | |
| Test Samples | | 0.1% $Na_2S$ Appearance | Appearance | Corrosion weight-loss |
| Example 1 | 39.0 at % Pt—Fe | ○ | ○ | 0 g/m³/hr |
| Example 2 | 39.1 at % Pt—0.5 at % Nb—Fe | ○ | ○ | 0 |
| Comparative 1 | $Sm_2Co_{17}$ type magnet (no coating) | ○ | x | 33 |
| Comparative 2 | $Sm_2Co_{17}$ type magnet Ni plating | x | Δ | 0 |
| Comparative 3 | Pure nickel | x | ○ | 0 |
| Comparative 4 | Fe—Cr—Co based magnet | ○ | x | 18 |

○ Good surface
Δ Weak discoloration
x Discoloration

COMPARATIVE EXAMPLES

The comparative samples were prepared from the following materials: (1) $Sm_2Co_{17}$ type rare-earth magnet without surface coating; (2) $Sm_2Co_{17}$ type rare-earth magnet with 20 μm thick Ni plating; (3) pure Ni; and (4) spinodal magnet containing 25 wt. % Cr, and 15 wt % Co, the balance being Fe. The samples 4 mm in length, 4 mm in width, and 3 mm in height were cut from each magnet. The process for forming the Ni plating on $Sm_2Co_{17}$ type magnet was: electrolytic degreasing the surface of the magnet; water rinsing; pickling; water-rinsing; Ni strike plating; water-rinsing; Ni plating; water-rinsing; and drying. The electrolytic degreasing was carried out by electrolyzing the sample as anode for 30 seconds in a solution (50° C.) containing 45 g/l of the degreasing liquid (commercially available Cleaner 160) under current density of 5 $A/dm^2$. The pickling was carried out by dipping the samples in liquid (room temperature), which was prepared by diluting the concentrated hydrochloric acid with twice volume of water. The Ni strike plating was carried out using a bath containing 200 g/l of $NiCl_2$ $6H_2O$ and 100 cc/l of HCl, at a current density of 5 $A/dm^2$ and for 90 seconds. The Ni plating was carried out using the so-called Watt bath at a current density of 5 $A/dm^2$. The bath contained 280 g/l of $Nicl_2 6H_2O$ 50 g/l of $Nicl_2$·$H_2O$ and 45 g/l of boric acid. The 20 μm thick Ni was electrolytically deposited.

The samples, except the Ni plated one, were polished with No. 1200 emery paper so as to smooth the surface before the corrosion test.

EXAMPLE 2

The process of Example 1 was repeated except that the composition was 39.1 atomic % of platinum, 0.5 atomic % of niobium, the balance being iron.

The magnetic properties were as follows: 10.0 kG of residual flux density; 4.5 kOe of coercive force; and, 20 MGOe of maximum energy product.

In addition to the tests carried out in Example 1, a precise analysis was carried out using an inductivity coupled plasma (ICP) emission spectrometer. The samples were dipped in various corrosive solutions, which simulate the environment in the mouth, so as to re-confirm the effectiveness of corrosion resistance of the magnet used in the present invention. The quantity of the ions dissolved into the solutions was measured by the ICP emission spectrometer.

The results are shown in Tables 2 and 3.

TABLE 2

Quantity of Dissolved Ions in Corrosive Solutions ($\mu g/cm^2/72$ Hrs)

|  | Platinum Magnet | | | 26% Cr—1% Mo Stainless Steel | | |
| --- | --- | --- | --- | --- | --- | --- |
|  | Pt | Fe | Nb | Fe | Cr | Mo |
| 1% NaCl | <0.5 | 0.5 | <0.5 | 0.6 | <0.5 | <0.2 |
| 0.05% HCl | <0.5 | 1.5 | <0.5 | 1.2 | <0.5 | <0.2 |
| 1% lactic acid | <0.5 | 1.6 | <0.5 | 1.6 | <0.5 | <0.2 |
| 0.1% $Na_2S$ | <0.5 | 0.9 | <0.5 | 0.9 | <0.5 | <0.2 |
| Artificial Saliva | <0.5 | 0.8 | <0.5 | 0.4 | <0.5 | <0.2 |

Remarks 1) < indicates that the quantity is less than the quantitative minimum value.
Remarks 2) The artificial saliva was Greenwood liquid and was prepared by dissolving in 1000 ml of distilled water 2.4 g of KCl, 0.6 g of $Ca_3(PO_4)_2$, $Na_3PO_4$, and 5.0 g of albumin. Before using, $CO_2$ gas was blown into the so-prepared solution to adjust pH to 6.7.
Remarks 3) The samples were subjected to wet-polishing with No. 800 emery paper, water rinsing, ultrasonic degreasing in acetone, and drying.
Remarks 4) The samples were subjected to corrosion at 37 ± 2° C. for 72 hours.

TABLE 3

Quantity of Ions Dissolved at the State of Magnetic Retention ($\mu g/cm^2/72$ Hrs)

|  | Platinum Magnet | | | 26% Cr—1% Mo Stainless Steel | |
| --- | --- | --- | --- | --- | --- |
|  | Pt | Fe | Nb | Cr | Mo |
| 1% NaCl | <0.5 | 0.5 | <0.5 | <0.5 | <0.2 |
| 0.05% HCl | <0.5 | 1.1 | <0.5 | <0.5 | <0.2 |
| 1% lactic acid | <0.5 | 2.0 | <0.5 | <0.5 | <0.2 |
| 0.1% $Na_2S$ | <0.5 | 0.5 | <0.5 | <0.5 | <0.2 |
| Artificial Saliva | <0.5 | <0.5 | <0.5 | <0.5 | <0.2 |

Corrosive condition is immersion for 72 hour at 37 ± 2° C.

TABLE 4

Samples of the Quantity of Dissolved Ions ($\mu g/cm^2/72$ Hrs)

|  | Sm—Co based type Rare Earth Magnet | |
| --- | --- | --- |
|  | Co | Sm |
| 1% NaCl | 20.6 | 0.8 |
| 0.05% HCl | 407.1 | 144.0 |
| 1% lactic acid | 242.0 | 144.0 |
| 0.1% $Na_2S$ | <0.08 | <0.3 |
| Artificial Saliva | 0.7 | 0.3 |

Corrosive condition is the same as in Table 2.
Remarks. This data is extracted from T. NAKANO, O. OKUNO, H. HAMANAKA: REPORTS OF THE ISTITUTE FOR MEDICAL & DENTAL ENGINEERING 22, (1989) p. 17.

It is apparent from Table 2 showing the result of the test for subjecting the platinum magnet and stainless steel separately to the corrosion test that the ions dissolved from the platinum magnet and the 26 % Cr - 1 % Mo stainless steel used as the root cap is a trace amount as small as approximately 2 $\mu g/cm^2/72$ Hrs.

It is apparent from Table 3 showing the result of the test subjecting the magnetically retentioned platinum magnet and stainless steel to the corrosion test that the ions dissolved from the platinum magnet and the 26 % Cr - 1 % Mo stainless steel used as the root cap is a trace amount as small as approximately 2 $\mu g/cm^2$ and is, in fact, very small even in the case that the two materials are magnetically retentioned with one another.

Figure 2:
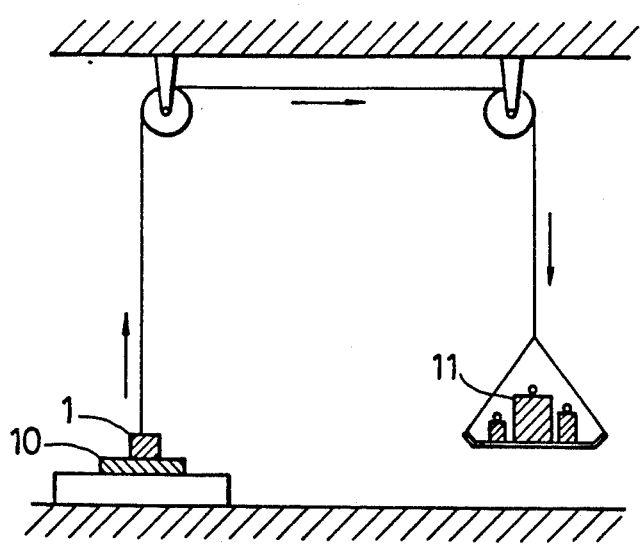
FIG. 2 shows the embodiment of a device for measuring the magnetic retention.

In order to prove the effectiveness of the denture-fixing method according to the present invention, the retention was measured by the method illustrated in FIG. 2. The 26 % Cr - 1 % Mo stainless steel 10 and the platinum magnet 1 were sized to be capable of mounting in a denture. They (1, 10) were brought into contact with one another in such a manner that the magnet 1 is fixed to the root cap; the retention between them was measured. The results are shown in Table 5.

TABLE 5

Measurement of Magnetic Retention

| | | Magnet Size (mm) | Magnet Volume (mm³) | Magnetic Retention Measurement in Open Magnetic Circuit | Magnetic Retention Measurement in Closed Magnetic Circuit |
|---|---|---|---|---|---|
| Example A | 39.1 at % Pt—0.5 at % Nb—Fe | 4φ × 3.5 H | 44.0 | 157 | — |
| Example B | 39.1 at % Pt 0.5 at % Nb—Fe | 2 T × 4 W × 3 H | 24.0 | 119 | 302 |
| Comparative C | $Sm_2Co_{17}$ type Rare Earth Magnet | 5.2φ × 2.0 H | 42.5 | — | 170 |
| Comparative D | $Sm_2Co_{17}$ type Rare Earth Magnet | 4.5φ × 2.5 H | 39.7 | — | 250 |

Figure 3:
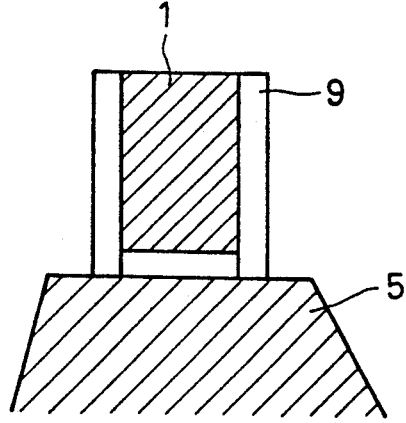
FIG. 3 illustrates an example of a fixing method.

Remarks
1) In the measurement in open circuit the retention measured is one required for separating the magnet from the root cap, to which the magnet is directly retentioned. In this case, the flux of magnetic force is not utilized for the retention but dissipates on the top of the magnet, so that the retention efficiency is low.
2) The measurement in closed circuit is shown in FIG. 3. The yokes 9 consist of the same material as the root cap 5, i.e., 26% Cr—1% Mo stainless steel. The yokes 9 are 1.5 mm in thickness, 4 mm in width, and 5 mm in height. The magnet 1 is sandwiched and bonded between the yokes 9. The N and S poles are formed on the sides of the magnet 1 facing the yokes 9. The organic binder can be used for attaching the magnet to the denture. The force measured is the one required for separating the yokes 9 from the root cap 5. Since the flux of magnetic force entirely enters the root cap 2 via the yokes 9, the retention efficiency is high. Since the magnetic circuit is closed, the magnetic leakage, which might be detrimental to a human body, does not occur.
3) Data in the comparative examples C, D are extracted from Ron Highton et al: The Journal of Prosthetic Dentistry, Vol. 56, No. 1, P. 104 (1986).

As is described hereinabove, the magnet used in the present invention is advantageous for fixing a denture from the points of view of magnetic properties and corrosion resistance.

We claim:

1. A method for fixing a denture comprising:
   attaching a non-plated magnet containing from 33 to 47 atomic % of platinum, the balance being iron, to an inner surface or lower surface of the denture;
   embedding in a tooth root a root cap consisting of soft magnetic, Fe-Cr based stainless steel; and,
   generating magnetic retention between the magnet and the root cap, thereby fixing the denture to the root cap.

2. A method according to claim 1 further comprising: magnetizing opposed surfaces of the magnet; covering said opposed surfaces of the magnet with yokes for forming a pass of magnetic flux, consisting of the same material as the root cap; bringing an end of the yokes into contact with the root cap, thereby forming a closed circuit of the magnetic flux through the magnet, the yoke and the root cap.

3. A method for fixing a denture comprising:
   attaching a non-plated magnet containing from 33 to 47 atomic % of platinum, and from 0.1 to 10 atomic % of at least one element selected from the group consisting of Ti, Mo, Nb, Ta, W, Cr, and V, the balance being iron, to an inner surface or lower surface of the denture;
   embedding, in a tooth root, a root cap consisting of soft magnetic, Fe-Cr based stainless steel; and,
   generating magnetic force between the magnet and the root cap, thereby fixing the denture to the root cap.

4. A method according to claim 3 further comprising: magnetizing opposed surfaces of the magnet; covering said opposed surfaces of the magnet with yokes for forming a pass of magnetic flux, consisting of the same material as the root cap; bringing an end of the yokes into contact with the root cap, thereby forming a closed circuit of the magnetic flux through the magnet, the yoke and the root cap.

5. A device for fixing a denture comprising:
   a non-plated magnet including means for mounting said magnet in a denture, a root cap including means for mounting said root cap in a tooth-root, said magnet being attachable to an inner or lower surface of the denture and containing from 33 to 47 atomic % of platinum, the balance being iron; and the root cap consisting of sort magnetic, Fe-Cr based stainless steel.

6. A device according to claim 5, wherein said magnet further contains from 0.1 to 10 atomic % of at least one element selected from the group consisting of Ti, Mo, Nb, Ta, W, Cr, and V.

7. A device according to claim 5 or 6, further comprising yokes, which yokes: cover opposed surfaces of the magnet; consist of the same material as that of the root cap; and, can be brought into contact with the root cap, the magnet, yokes, and root cap forming a closed circuit of magnetic flux.

* * * * *